(12) United States Patent
James et al.

(10) Patent No.: US 8,116,855 B2
(45) Date of Patent: Feb. 14, 2012

(54) FETAL SURVEILLANCE

(75) Inventors: David Keith James, Wysall (GB); John Andrew Crowe, West Bridgford (GB); Barrie Robert Hayes-Gill, Radcliffe on Trent (GB); Carl William Barratt, Pentrich (GB); Jean-Francois Pieri, Nottingham (GB)

(73) Assignee: Monica Healthcare Limited, Nottingham (GB)

( * ) Notice: Subject to any disclaimer, the term of this patent is extended or adjusted under 35 U.S.C. 154(b) by 0 days.

(21) Appl. No.: 10/595,378

(22) PCT Filed: Oct. 13, 2004

(86) PCT No.: PCT/GB2004/004315
§ 371 (c)(1),
(2), (4) Date: Nov. 27, 2006

(87) PCT Pub. No.: WO2005/039410
PCT Pub. Date: May 6, 2005

(65) Prior Publication Data
US 2007/0213627 A1    Sep. 13, 2007

(30) Foreign Application Priority Data

Oct. 14, 2003 (GB) .................................. 0324018.1
Oct. 16, 2003 (GB) .................................. 0324196.5

(51) Int. Cl.
*A61B 5/04* (2006.01)
(52) U.S. Cl. .......................... 600/509; 600/511; 600/515
(58) Field of Classification Search .................. 600/509, 600/511, 515, 508
See application file for complete search history.

(56) References Cited

U.S. PATENT DOCUMENTS

| | | | | |
|---|---|---|---|---|
| 3,989,034 A | * | 11/1976 | Hojaiban | 600/511 |
| 4,211,237 A | * | 7/1980 | Nagel | 600/511 |
| 4,573,479 A | * | 3/1986 | Tuccillo | 600/511 |
| 4,781,200 A | | 11/1988 | Baker | |
| 4,945,917 A | * | 8/1990 | Akselrod et al. | 600/509 |
| 4,951,680 A | * | 8/1990 | Kirk et al. | 600/511 |
| 5,088,498 A | * | 2/1992 | Beach et al. | 600/453 |
| 5,596,993 A | * | 1/1997 | Oriol et al. | 600/511 |
| 5,666,959 A | * | 9/1997 | Deans et al. | 600/511 |
| 5,957,855 A | | 9/1999 | Bennett et al. | |

(Continued)

FOREIGN PATENT DOCUMENTS

WO    00/54650 A    9/2000

(Continued)

OTHER PUBLICATIONS

Oostendorp et al., "The fetal ECG throughout the second half of gestation", Clinical Physics and Physiological, Measurement, vol. 10, No. 2, pp. 147-160 (1989).

(Continued)

*Primary Examiner* — Niketa Patel
*Assistant Examiner* — Nicole F Lavert
(74) *Attorney, Agent, or Firm* — Momkus McCluskey, LLC; Jefferson Perkins

(57) ABSTRACT

The spatial position of a fetus within the womb is determined and monitored through analysis of ECG waveform data received from a set of electrodes that are attached to a maternal abdomen in a predetermined configuration. The waveform is compared with a set of predefined stored templates to determine the position of the fetus. An event logger may determine the number of fetal movements during a period of time.

39 Claims, 8 Drawing Sheets

U.S. PATENT DOCUMENTS

| | | | | |
|---|---|---|---|---|
| 6,115,624 A * | 9/2000 | Lewis et al. | | 600/376 |
| 6,551,251 B2 * | 4/2003 | Zuckerwar et al. | | 600/528 |
| 6,669,653 B2 * | 12/2003 | Paltieli | | 600/588 |
| 2001/0014776 A1 * | 8/2001 | Oriol et al. | | 600/511 |
| 2004/0073094 A1 * | 4/2004 | Baker | | 600/300 |
| 2004/0243015 A1 * | 12/2004 | Smith et al. | | 600/511 |
| 2005/0267376 A1 * | 12/2005 | Marossero et al. | | 600/511 |

FOREIGN PATENT DOCUMENTS

| | | |
|---|---|---|
| WO | 01/26545 A1 | 4/2001 |
| WO | 03/055386 A1 | 7/2003 |

OTHER PUBLICATIONS

Roche et al., "The fetal electrocardiogram V. Comparison of lead systems", American J. of Obstetrics & Gynecology, vol. 92, No. 8, pp. 1149-1159 (1965).

"AOCG practice bulletin—Antepartum fetal surveillance", International J. of Gynaecology & Obstetrics 68:175-186 (2000).

Dawes et al., "Computerized evaluation of fetal heart-rate patterns", J. of Perinatal Medicine 22:491-499 (1994).

Clark et al., "Nonstress testing with acoustic stimulation and amniotic fluid volume assessment: 5973 tests without unexpected fetal death", American J. Obstetrics & Gynecology 160:694-697 (1989).

Manning et al., "Fetal biophysical profile scoring: selective use of the nonstress test", American J. of Obstetrics & Gynecology 156:709-712 (1989).

Erskine et al., "Umbilical artery blood flow characteristics in normal and growth-retarded fetuses", British J. of Obstetrics & Gynecology 92:605-610 (1985).

Moore et al, "A prospective evaluation of fetal movement screening to reduce the incidence of antepartum fetal death", American J. of Obstetrics & Gynecology 160:1075-1080 (1989).

Neldam, "Fetal movements as an indicator of fetal well-being", Danish Medical Bulletin 30:274-278 (1983).

Shono et al., "Fetal heart rate recorder for long-duration use in active full-term pregnant women", Obstetrics & Gynecology vol. 83, No. 2, p. 301 (1994).

De Vries et al., "The emergence of fetal behaviour I. Qualitative Aspects", Early Human Development 7:301-322 (1982).

Hayes-Gill, Barrie et al., "Ante-natal Heart Rate Recorder for Continuous Assessment of Fetal Health", Mar. 18, 2003, XP002312986, downloaded from http://www.eee.nott.ac.uk/medical/heart/c2000/Care2000ver9_180803.pdf on Jun. 21, 2006.

Rabinowitz, R. et al., "The relation between fetal heart rate accelerations and fetal movements", Obstetrics and Gynecology vol. 61, No. 1, pp. 16-18 (Jan. 1983), XP008041332.

European Patent Office acting as the ISA/EP, International Search Report for PCT/GB2004/004315, Jan. 13, 2005.

European Patent Office acting as the ISA/EP, Examination Report for Appl. No. 00966289.1-2305, Oct. 24, 2006.

European Patent Office acting as the ISA/EP, Examination Report for Appl. No. 00966289.1-2305, Aug. 18, 2006.

European Patent Office acting as the ISA/EP, Examination Report for Appl. No. 00966289.1-2305, Mar. 29, 2006.

European Patent Office Search Report for Appl. No. EP 07 01 2903, May 28, 2008.

James et al., "Neurobehavioral Development in the Human Fetus", Fetal Development. A Psychobiological Perspective, 1995, p. 101-128, Lawrence Erlbaum Associates, Inc., Hillsdale, NJ.

\* cited by examiner

Figure 1: The Five Fetal Presentations

Figure 2: The Six Positions in Vertex Presentations

Figure 3: Cross-sectional diagram of the Six Vertex Positions

Figure 4: Typical Adult ECG

Figure 5: Fetal ECG Complexes for the Determination of Fetal Movements

Figure 6: ECG Waveform recorded on the Maternal Abdomen

Figure 7: Midline Electrode Configuration

FETAL SURVEILLANCE

The present invention relates to apparatus and a method for detecting both the spatial and temporal behaviour of a fetus.

It is useful to be able to quantify the degree of movement of a fetus within the uterus as this can provide information regarding the health of the fetus during the progress of pregnancy. In addition, knowing the current position and presentation of the fetus within the uterus can provide information regarding presentation of the fetus. Currently there are several techniques applied to Antepartum fetal surveillance in order to assess fetal health. These techniques include:

Contraction Stress Test
Nonstress Test
Fetal movement assessment
Biophysical Profile
Modified Biophysical Profile
Umbilical Artery Doppler Velocimetry The Contraction Stress Test (CST) uses Doppler Ultrasound to measure fetal heart rate and is based on the response of the fetal heart rate to uterine contractions. The technique works on the principle that fetal oxygenation will momentarily deteriorate as a consequence of uterine contractions. Under certain conditions, for example in the sub-optimally oxygenated fetus, the resultant intermittent deterioration in oxygenation of the fetus will modify the fetal heart rate pattern in a manner which enables diagnosis of the condition. Several techniques can be used to induce uterine contractions including nipple stimulation and intravenous administration of dilute oxytocin. Such techniques are described in the document entitled "AOCG practice bulletin—Antepartum fetal surveillance", from the International Journal of Gynaecology & Obstetrics, 2000, 68, pages 175 to 186.

The Nonstress Test (NST) provides a measure of variation in the fetal heart rate since heart rate reactivity is considered to be a good indicator of autonomic function in the healthy fetus. NST is based on the premise that the heart rate of a healthy fetus will undergo temporary accelerations coincident with fetal movement. With the mother in the lateral tilt position, the fetal heart rate trace is typically examined for accelerations which peak at least 15 beats per minute above baseline for a period of 15 seconds, measured baseline to baseline. Furthermore, others have attempted to computerise such analysis, a process described in the document entitled "Computerized evaluation of fetal heart-rate patterns", by Dawes et al from the Journal of Perinatal Medicine, 1994, 22, pages 491 to 499. Typically the fetal heart rate itself would be determined using Doppler Ultrasound techniques.

A variation on the NST technique employs acoustic stimulation of the fetus to induce fetal heart rate accelerations which has the effect of reducing overall NST testing-time. In this context, acoustic stimulation is applied using a purposely-designed loudspeaker positioned on the maternal abdomen, sometimes referred to as an artificial larynx. This process is described in the document entitled "Nonstress testing with acoustic stimulation and amniotic fluid volume assessment: 5973 tests without unexpected fetal death", by Clark et al from the American Journal of Obstetrics and Gynaecology, 1989, 160, pages 694 to 697. The results of this test are interpreted to determine whether the fetus is reactive or non-reactive according to pre-determined criteria.

An evaluation of fetal movement is also considered a valuable indicator of fetal health. This technique is based on the premise that a decrease in fetal movement is often seen as a precursor to fetal death, sometimes by several days. There are several methods which are currently employed to quantify fetal movements, more specifically: "kick counts" as perceived by the mother; Ultrasound imaging and Doppler ultrasound.

The Biophysical Profile (BPP) comprises a Nonstress test as described previously along with four additional observations of the fetus which are facilitated using real-time Ultrasound Imaging. Consequently, the Biophysical Profile comprises five parts, each of which are assigned a score. These scores are then added to derive a composite score which is compared with a predetermined 'normal' score to provide a measure of fetal health. The BPP assessment comprises: NST; observation of fetal breathing movements; observation of fetal body and limb movements; observation of the extension of fetal extremities; and determination of the amniotic fluid volume. This process is described in the document entitled "Fetal biophysical profile scoring: selective use of the nonstress test", by Manning et al from the American Journal of Obstetrics and Gynaecology, 1987, 156, pages 709 to 712.

The modified Biophysical Profile (mBPP) is based on the premise that assessment of the Amniotic fluid volume can be used to evaluate long-term placental function. The 'Amniotic Fluid Index' is derived from the sum of measurements of the amniotic fluid pockets in each of the abdominal quadrants. Gauging the Amniotic Fluid Index In combination with a Nonstress test forms the modified Biophysical Profile and provides a measure of general fetal well-being. This process is described in the document entitled "AOCG practice bulletin—Antepartum fetal surveillance", from the International Journal of Gynaecology & Obstetrics, 2000, 68, pages 175 to 186.

Umbilical Artery Doppler Velocimetry employs Ultrasound Imaging to assess the flow velocity in the umbilical artery of a fetus. Primarily, this technique aims to identify the disparity between the flow velocity waveforms observed in the umbilical artery of the normal fetus and those observed in the intrauterine growth restricted fetus. More specifically, in the normal fetus the diastolic flow velocity is relatively high, where in the growth-restricted fetus this rate of flow is attenuated. This process is described in the document entitled "Umbilical artery blood flow characteristics in normal and growth-retarded fetuses", by Erskine et al, from the British Journal of Obstetrics and Gynaecology, 1985, 92, pages 605 to 610.

The first aspect of this invention is concerned with one approach to fetal surveillance, more specifically, the assessment of fetal movements. Current techniques used to quantify fetal movements are:

"kick counts"
Doppler ultrasound
Ultrasound imaging

It has been known for centuries that the mother is capable of perceiving fetal movements, more recently it became clear that the mothers perception of "diminished fetal activity" should be regarded as a worrying sign. As such, Fetal "kick counts" as perceived by the mother are a recognised technique for determining the motility of the fetus. Several counting protocols have been applied in an attempt to quantify these movements, in one of the most popular, the mother lies on her side and counts distinct fetal movements. This process is described in the document entitled "A prospective evaluation of fetal movement screening to reduce the incidence of antepartum fetal death", by Moore et al from the American Journal of Obstetrics and Gynaecology, 1989, 160, pages 1075 to 1080. Perception of ten or more distinct movements over a period of 2 hours is considered reassuring. In another approach, the mother counts fetal movements for one hour three times a week, a process described in the document entitled "Fetal movements as an indicator of fetal well-being" by Neldam from the Danish Medical Bulletin, 1983, 30, pages 274 to 278. In this instance a reassuring count is considered to be one which equals or exceeds the previous count. This technique is simple to implement, but is largely considered a pre-cursor to further fetal assessment in the absence of a reassuring count.

The Doppler ultrasound technique consists of directing a 2 MHz (or other similar frequency) crystal transducer at the fetus on the mother's abdomen. The signal reflected from the fetus is shifted by a small frequency (known as the Doppler shift) which is due to movements of, or within, the fetus. In its customary role Doppler ultrasound is employed to identify pulsations of the fetal heart in order that (after suitable processing) a fetal heart rate (fHR) trace can be produced. However, the Doppler ultrasound technique itself can be employed to identify all movements in its path including fetal body movements, limb movements and breathing movements. In its normal mode of operation as a fHR recorder, the reflected Doppler signal is filtered to remove frequencies which appear outside of the range into which the fetal heart rate will fall. Signals relating to fetal movements however, are generally evident outside of this frequency range. Therefore, in the event that the Doppler signal is filtered to cover a different frequency range i.e. signals which are reflected at other frequencies, it is possible to use the technique to identify fetal movements. Such a system, using an adaptation of a conventional Doppler ultrasound unit, has been developed and is described in the document entitled "Neurobehavioral development in the human fetus" by James et al, Fetal Development—A Psychobiological Perspective, 1995, pages 101 to 128. A limitation of the Doppler Ultrasound technique is apparent in single channel Doppler systems which require periodic re-positioning of the transducer to point at the fetus as it moves around the uterus, this requires the intervention of clinically trained staff. In addition to prevent the transducer from moving over the mothers abdomen it is held in place with a belt which can prove to be uncomfortable for the mother. A multi-channel Doppler ultrasound unit has also been described in the document entitled "Fetal heart rate recorder for long-duration use in active full-term pregnant women", by Shono et al from Obstetrics and Gynaecology, 1994, 83, 2, page 301. This consists of six Doppler transducers positioned on the abdomen with each being optimally positioned for the various stances of the mother during her day. However, due to the nature of the ultrasound signal being directed at the fetus then long-term recordings of fHR using ultrasound may be considered to be invasive. Although this invasive nature has not been clinically substantiated, the bulky instrumentation and restraint belts necessary to implement the technique mean that the use of Doppler ultrasound is still limited to short time periods. In summary, Doppler Ultrasound can be used to monitor fetal movements and to produce an "actogram" or "fetal movement profile" which identifies fHR and fetal movement over short time periods.

The development of Ultrasound Imaging proved to be the catalyst to much greater understanding of fetal movements than was previously the case. This technique is non-invasive and enables images of organs and structures within the human body to be displayed on a monitor, illustrating for example the location and size of a structure without the necessity for surgery.

Ultrasound Imaging enables specific fetal movements to be isolated and defined, more particularly: fetal body movements; fetal limb movements; fetal mouthing; fetal eye movements and fetal diaphragmatic movements. Fetal body and limb movements are arguably the most important variables to monitor in an assessment of fetal health. One definition of 'normal' fetal activity cites three or more discrete body or limb movements within thirty minutes to be acceptable. Fetal eye and mouthing movements are another commonly observed indication of fetal activity, indeed it has been suggested that mouthing movements are a good discriminator of fetal acidosis. Diaphragmatic movements of the fetus typically refer to fetal breathing but can also include movements which have been described as sighs or hiccups. Definitions as to what is acceptable in this context vary but it is typically quantified as one or more episodes of fetal breathing movements in excess of thirty seconds within a time window of thirty minutes.

Typically, information gathered during Ultrasound Imaging will be presented in the form of an actogram, which displays all of the individual components of fetal movement along with a simultaneously recorded fHR trace plotted against a time axis. Whilst Ultrasound Imaging provides detailed information about fetal movement, it is limited to hospital use by the sheer size of the instrumentation itself and the necessity for highly trained clinicians to supervise its operation.

Many years ago it was believed that all motor behaviour of the fetus was the result of a known or unknown stimulus. Latterly, with the onset of Ultrasound Imaging enabling the fetus to be observed in its own environment it was demonstrated that specific movement patterns remain recognisable throughout gestation and that they show clear developmental trends, which supports the view that fetal motility is generated spontaneously by the fetal central nervous system and as such is one of the fundamental expressions of early neural activity as described in the document entitled "The emergence of fetal behaviour I. Qualitative Aspects" by de Vries et al from Early Human Development, 1982, 7, pages 301 to 322.

The greatest advantage of the fact that the fetus makes body movements could be considered to be the reassurance it provides to the mother. Though the presence of fetal movement alone cannot be considered a substantiation of fetal health, the cessation of these movements during gestation is considered a very worrying sign.

Randomised studies have demonstrated that records of fetal motility kept by the mother to record "kick counts" contribute to a decrease in fetal mortality as described in the document entitled "Fetal movements as an indicator of fetal well-being" by Neldam from the Danish Medical Bulletin, 1983, 30, pages 274 to 278. A more objective means of study is preferable since maternal perception of movements can vary depending on the motility of a given fetus and the degree of movement felt by a given mother.

Moreover, along with recording of fHR, screening for fetal movements is one of the main assessment methods for studying neurobehavioural development of the fetus.

The second aspect of this invention is concerned with a technique to determine fetal presentation and position during gestation.

Fetal presentation describes the orientation of the fetus within the maternal uterus in terms of the part of the fetus which lies at the pelvic brim and is thus positioned to enter the birth canal first. There are five recognised fetal presentations, these presentations, which are illustrated in FIG. 1 are:

Vertex, shown in FIG. 1(*a*)
Face, shown in FIG. 1(*c*)
Brow, shown in FIG. 1(*b*)
Breech, shown in FIG. 1(*d*)
Shoulder, shown in FIGS. 1(*e*) and (*f*)

Of these possibilities; Vertex, Face and Brow are also termed Cephalic presentations. A Vertex presentation is identified when the head of the fetus is flexed to leave the crown as the presenting part. Alternatively, when the head is extended, the Face of the fetus presents and when it is neither well flexed nor fully extended, the fetus has a Brow presentation. It is generally accepted that Cephalic presentation of this type is the most common form of fetal presentation, whilst Breech presentation occurs less frequently. A classical Breech presentation is identified when the buttocks of the fetus present first and both the hips and knees of the fetus are flexed. A Breech presentation also defines the circumstance where the hips of the fetus are flexed so that the legs are fully drawn toward the chest, or when the feet or knees present first. A Shoulder presentation occurs when the fetus is in a transverse lie, causing the shoulder, arm or trunk to exit the uterus first. Fetal position describes the rotational position of the fetus within the uterus for Vertex presentations only. The six fetal positions associated with the Vertex presentation and illustrated in FIG. 2 are: Right Occipitoanterior (ROA), FIG. 2(a); Right Occipitolateral (ROL), FIG. 2(c); Right Occipitoposterior (ROP), FIG. 2(e); Left Occipitoanterior (LOA), FIG. 2(b); Left Occipitolateral (LOL), FIG. 2(d) and Left Occipitoposterior (LOP), FIG. 2(f). Fetal position can be defined more accurately as the relationship between the fetus and six discrete points on the pelvic brim as illustrated in FIG. 3.

During gestation, fetal presentation and position are typically identified using palpation, i.e. manipulation of the maternal abdomen by a clinician or midwife to determine the fetal lie by feel alone. Alternatively, Ultrasound Imaging techniques are frequently employed to provide a more scientific indication of both fetal presentation and position within the maternal abdomen.

Additionally, several publications have highlighted differentiation between abdominal fetal ECG waveforms which appears to be dependent upon the presentation of the fetus. Specifically, the major deflections that can be identified in the abdominal fetal ECG coincident with the strike of the fetal heart (analogous to the QRS complex in adult ECG waveforms) in Breech presentation were more or less the inverse of those in a Vertex presentation. This observation is described in several documents, including that entitled "The fetal ECG throughout the second half of gestation", by Oostendorp et al from Clinical Physics and Physiological Measurement, 1989, 10, 2, pages 147 to 160 and also in the document entitled "The Fetal Electrocardiogram V. Comparison of lead systems", by Roche et al from the American Journal of Obstetrics and Gynaecology, 1965, 92, 8, pages 1149 to 1159.

Up to 14% of babies are in a breech presentation until the 29th to 32nd week of gestation. Many, but not all, of these babies change to a vertex presentation preceding birth. It is important that the fetus is in a Vertex or other Cephalic presentation pre-delivery to minimise the risk of asphyxia caused by cord strangulation, and to simplify delivery. Furthermore, considering fetal position, Occipitoanterior positions are often considered more favourable than Occipitoposterior positions. This is a consequence of the back of the fetus conforming with the concavity of the maternal abdominal wall hence allowing it to flex more readily. As a corollary of this, there is also a tendency for the head to flex, presenting a smaller diameter to the pelvic brim.

It is an object of the present invention to provide a method and apparatus for automatically monitoring fetal behaviour over a period of time. It is a further object of the present invention to provide a method and apparatus for automatically determining the presentation and/or position of the fetus in the abdomen.

Aspects of the invention are defined in the accompanying independent claims.

Embodiments of the present invention will now be described by way of example and with reference to the accompanying drawings in which.

In accordance with the first aspect of the invention we present a method to establish fetal well-being by quantifying fetal body movements both antenatally and intrapartum. The invention is based upon the identification of temporal and spatial variations in the fetal ECG shape which is detected using electrodes placed on the maternal abdomen.

Figure 1:
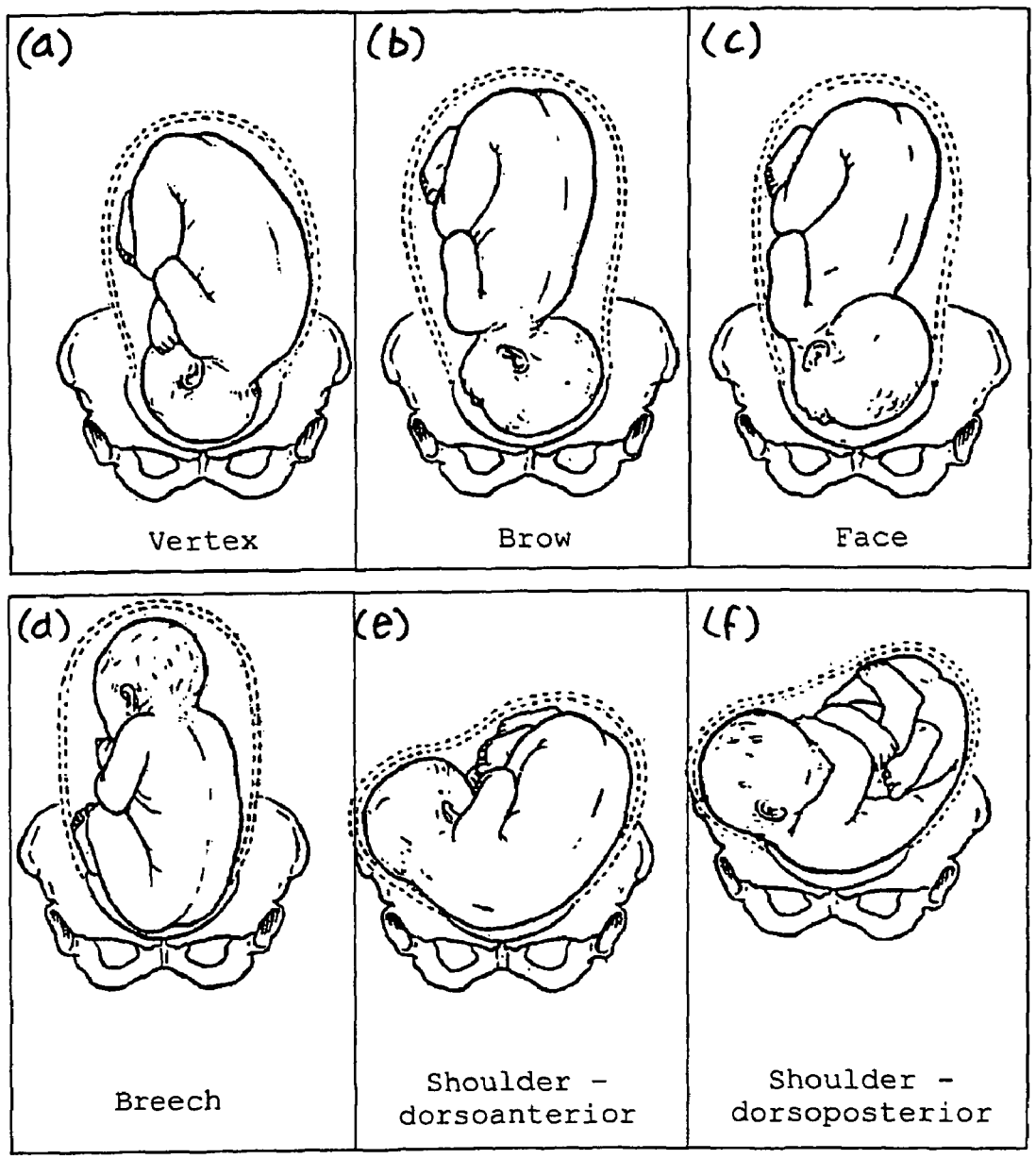
FIG. 1 illustrates five fetal presentations within the uterus.
Figure 2:
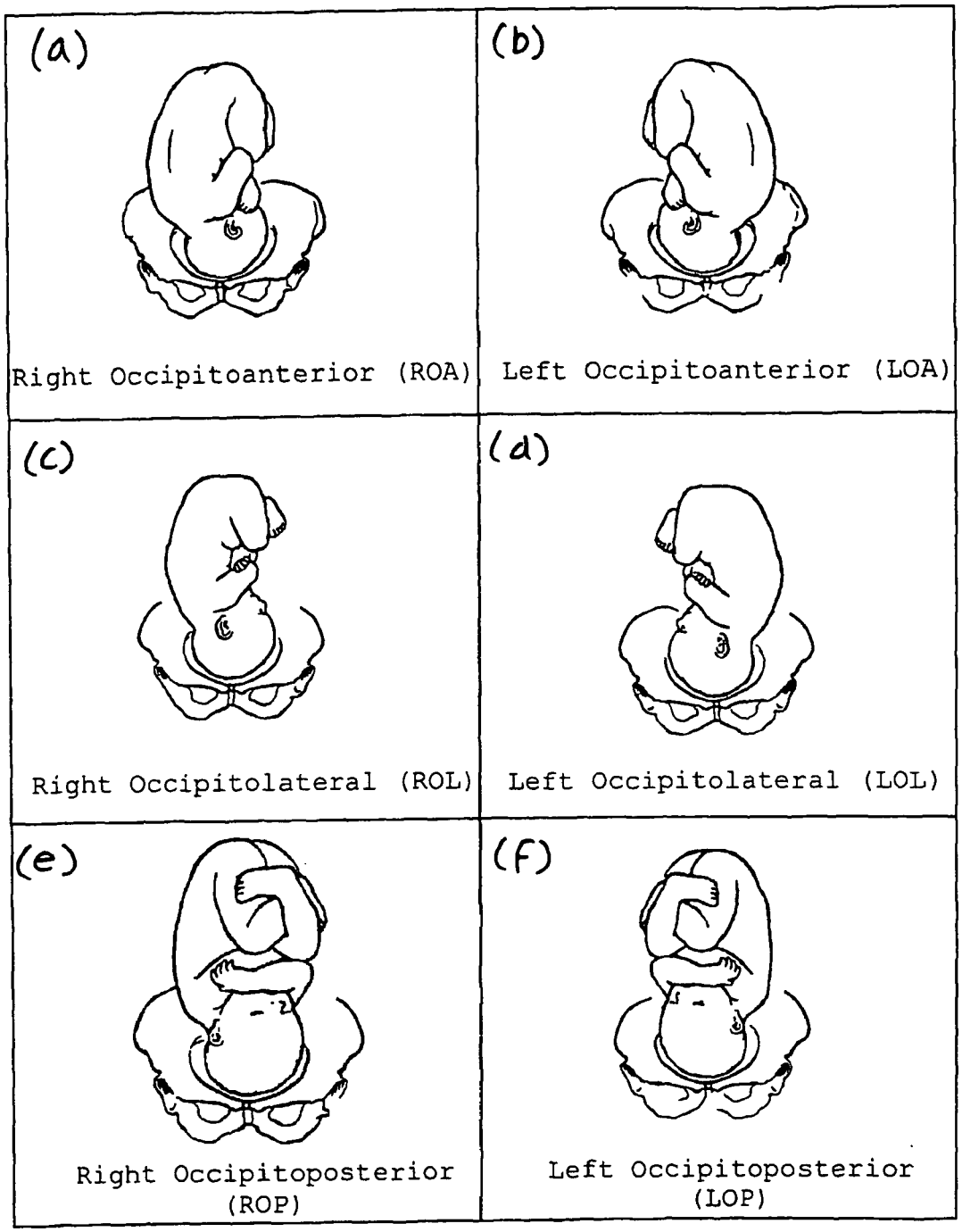
FIG. 2 illustrates six rotational positions of the fetus within the uterus corresponding to the vertex presentation of FIG. 1(a)
Figure 3:
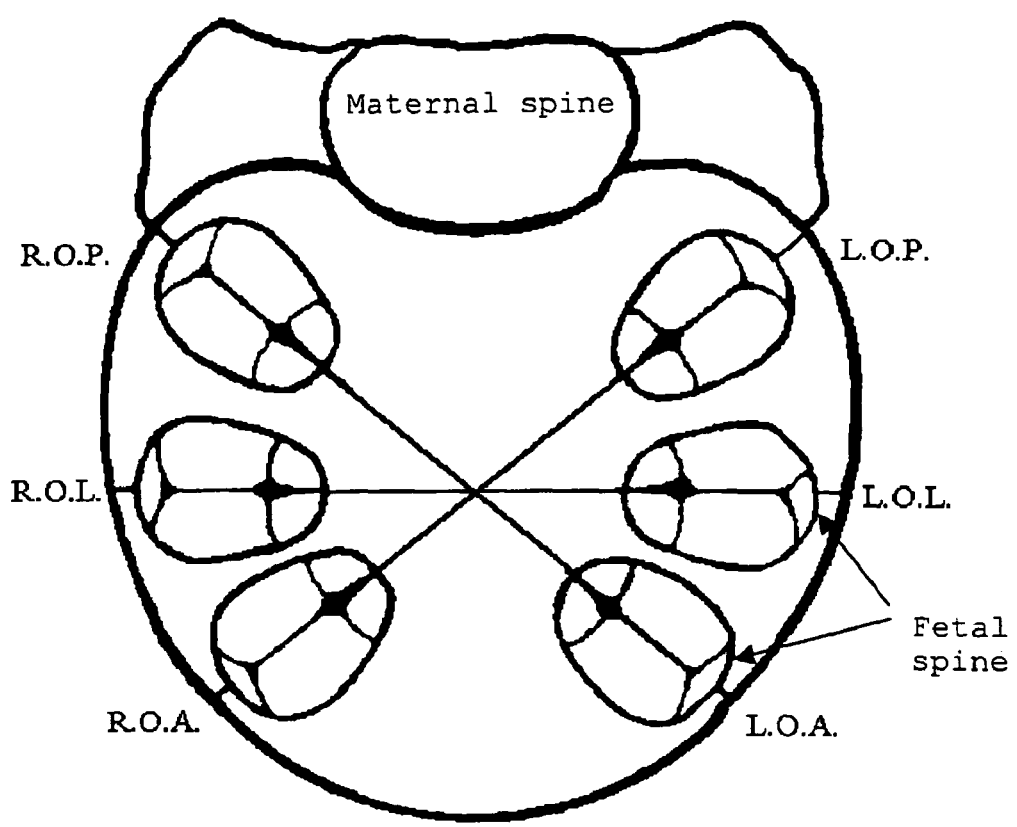
FIG. 3 illustrates in axial cross-sectional schematic view the six presentations of FIG. 2 relative to the pelvic brim.
Figure 4:
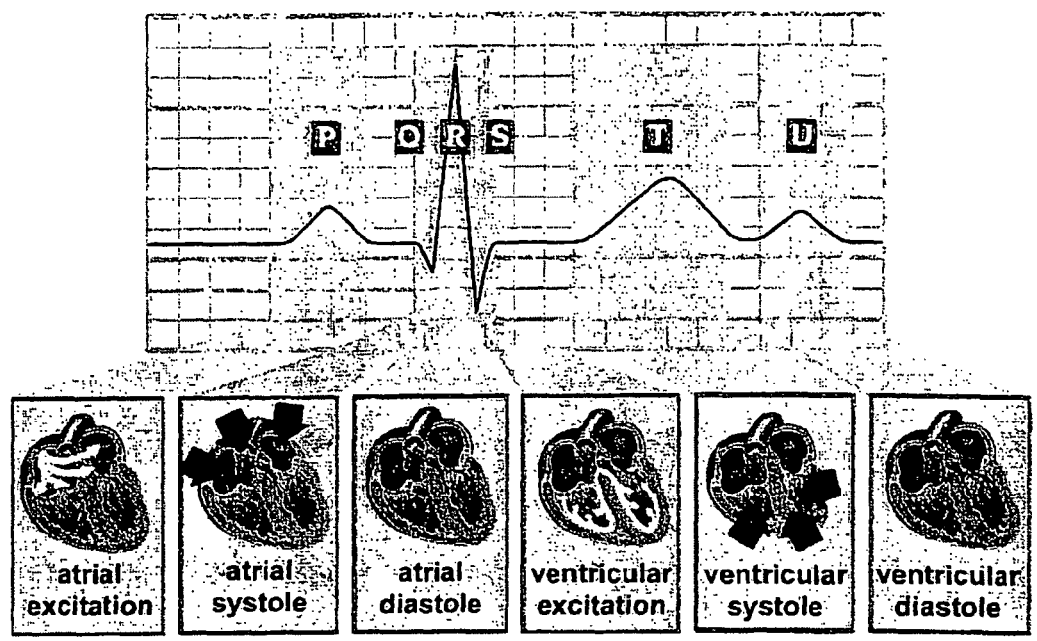
FIG. 4 illustrates a typical adult ECG complex waveform.

The ECG shape recorded from a typical adult heart using electrodes placed on the chest is shown in FIG. 4. The segment of waveform which is marked by the letters QR and S is termed the QRS complex and in general can be seen to follow the shape shown in FIG. 5c. In the event that the positions of the adult chest electrodes are reversed, i.e. their positions are rotated through 180°, the ECG which is generated becomes an inverse copy of the previous ECG. Accordingly, the QRS complex with the reversed electrode configuration assimilates to that shown in FIG. 5d. The action of rotating the position of the electrodes in this way is analogous in the context of abdominal fetal ECG to the fetus rotating through 180° within the maternal uterus. Furthermore, if the fetus performs an angular rotation of ±90° within the maternal uterus the fetal ECG will register an intermediate shape of the form illustrated in FIG. 5a or FIG. 5b. These four principal ECG complexes, shown in FIG. 5 and corresponding with fetal axial heart movements, are referred to as types A, B, C and D.

Figure 6:
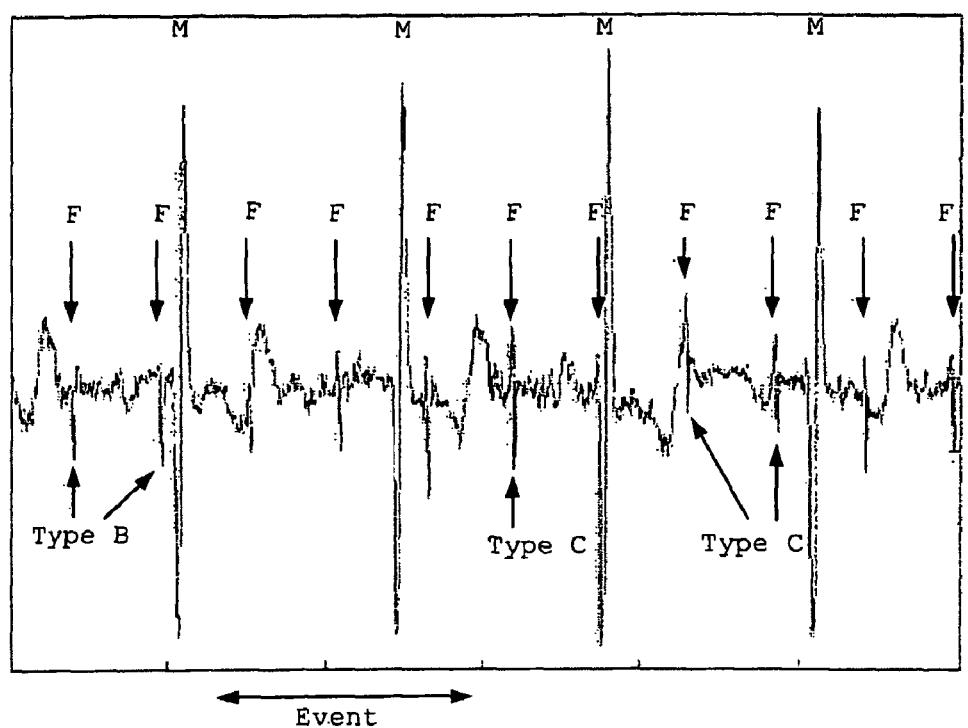
FIG. 6 illustrates a typical ECG waveform recorded from sensors positioned on the maternal abdomen.

A temporal example of transition between these ECG complexes in a real ECG recording detected using electrodes on the maternal abdomen is shown in FIG. 6. This signal comprises both the fetal ECG (F) and maternal ECG (M) and illustrates the chronological variation in electrical signals during a moment of fetal movement recorded by the mother. With due reference to FIG. 6, the actual fetal movement occurred during the time period labelled "Event". It can be seen that preceding the "Event" the fetal ECG shape assimilates to a complex of Type B, whilst after the "Event" the fetal ECG changes to Type C. During the "Event", which typically covers a period of around 1 second (referred to as transition time), it can be seen that the fetal ECG does not change from a Type B complex to Type C instantaneously; instead it passes through an intermediate shape part way between as the fetus continues to move. It will be realised that recording the number and frequency of these transitions over a given recording period (typically greater than 1 hour) will provide a measure of fetal activity and hence an indication of fetal well-being.

In accordance with a second aspect of the invention we provide a means to combine the identification of fetal body movements both antenatally and intrapartum as described in the first part of this invention, with fetal heart rate measured simultaneously using the same electrodes on the maternal abdomen.

Figure 7:
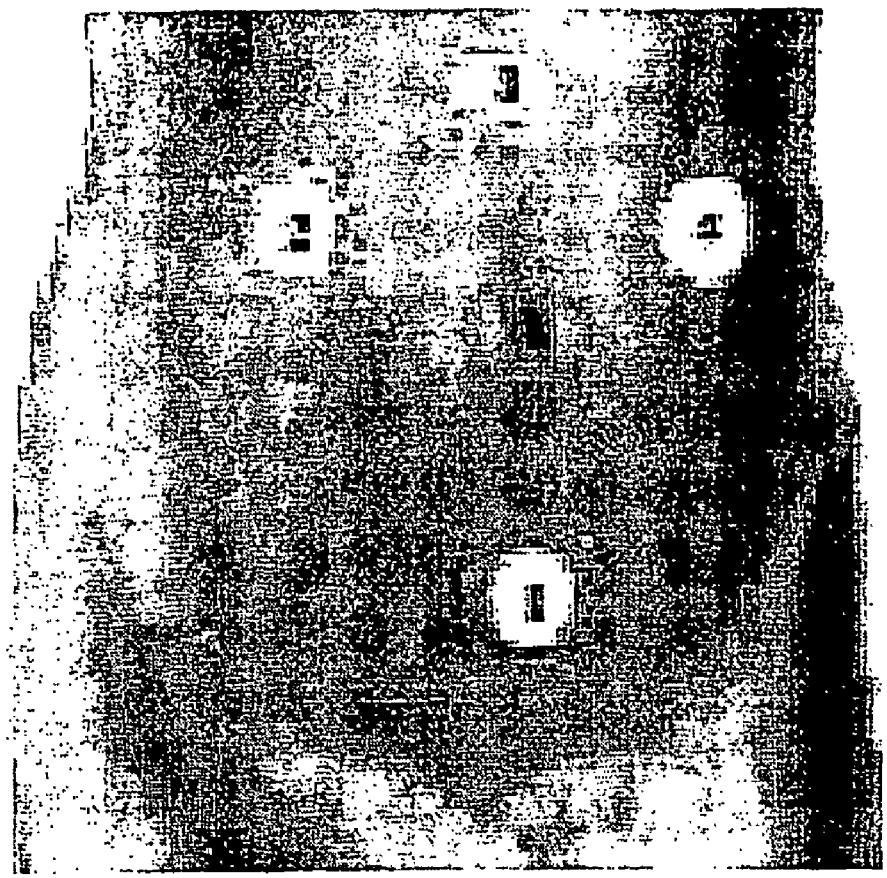
FIG. 7 illustrates a typical configuration of electrodes mounted on the maternal abdomen useful for monitoring fetal behaviour, presentation and position.

In accordance with a third aspect of the invention we provide a method of determining the spatial presentation and position of a fetus both antenatally and intrapartum. This technique is based upon a comparison of the complexes which appear within a particular fetal ECG waveform with complexes known to be coincident with a particular fetal position and presentation. To give an example, assuming the electrodes are placed in a midline configuration as shown in FIG. 7, a fetus in a Cephalic presentation will exhibit a fetal ECG complex of Type A, whilst those in a Breech presentation will exhibit a fetal ECG complex of Type B. A fetus in shoulder dorsoanterior or shoulder dorsoposterior presentations will display fetal ECG complexes of Type's C and D. The ability to detect fetal presentation in this way will typically provide the clinician, midwife and mother with information to aid the management of pregnancy, and for at-term mothers, the management of imminent labour.

All aspects of this invention rely upon the acquisition of a fetal ECG trace of acceptable quality. Accordingly, the method and apparatus described in patent application publication nos. WO2001/26545 (published), EP1220640 (published), and AU 200076734-A (abandoned), which facilitates the detection and extraction of high quality fetal ECG from electrodes placed on the maternal abdomen over long recording periods are suited to this purpose.

A computerised algorithm is applied to the captured fetal ECG signal in order to enable fetal movements to be quantified and fetal position and presentation to be accurately identified. Three techniques can be applied to achieve this, these are:

Template Matching
Phase Detection
Integration

The first of these techniques is based upon template matching. Typically, in this procedure, the maternal ECG is subtracted and a match filtering technique is carried out to locate the fetal ECG using a predefined template. The signal rings at the fetal ECG position and identifies the location of the fetal ECG signal in the time trace. This then allows a new fetal ECG template to be generated which may be the same shape as the original template or one of the four types of FECG complex types illustrated in FIG. 5. It is the number of fetal template changes that provides an indication pertaining to fetal movement, fetal position and fetal presentation from this trace. As previously described, the degree of fetal movement can be determined by counting the number of transitions (or fetal template updates) between ECG complex 'types' which occur within a given time frame, while fetal presentation and position can be determined by comparison of the ECG complex with the templates illustrated in FIG. 5.

Figure 5:
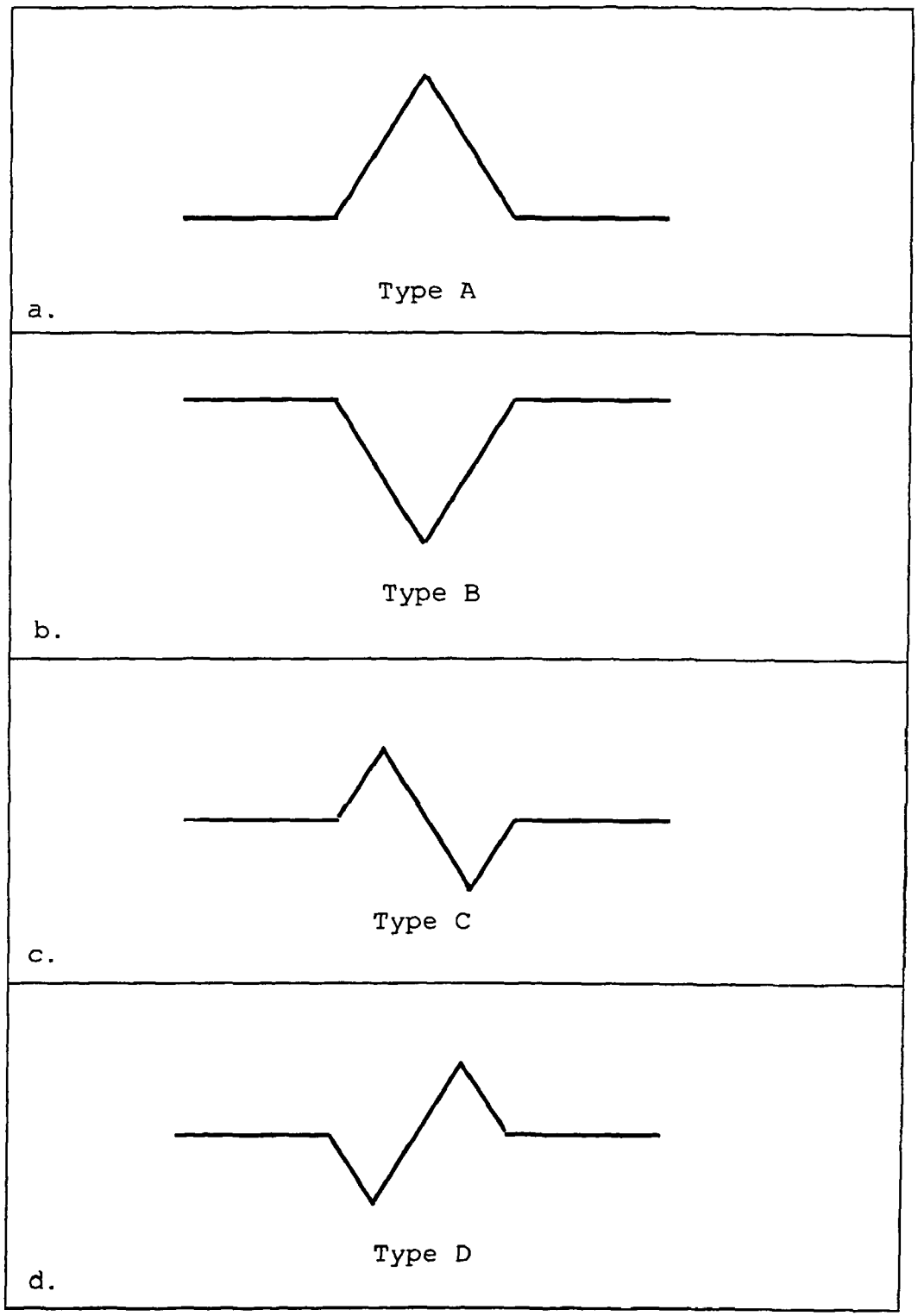
FIG. 5 illustrates exemplary fetal ECG complexes useful in determining fetal movements.

The second technique is based upon phase detection. FIG. 5 shows four basic fetal complexes which correlate with the direction of the fetal heart vector. It will be realised that these complexes could be assimilated to a standard sine wave and as such would exhibit a phase shift dependent upon the position of the fetal heart vector. The degree of fetal movement can be determined by counting the number of phase shifts which occur between subsequent fetal ECG complexes, whilst the phase angle itself provides an indication of fetal position and presentation.

The third technique is based upon integration. An average, or baseline, is established from the fetal ECG time trace, which is used as a reference. The fetal ECG complex is then integrated with respect to this baseline in order to establish how much "energy" in the complex is contained above and below the baseline. The degree of fetal movement can be determined by changes in the relative energy of the signal above and below the baseline within a given time frame.

The above techniques can be applied individually or, alternatively, a combination of any or all of the techniques can be applied to enable fetal movements to be quantified and fetal position and presentation to be identified from the captured fetal ECG signal.

Typically, a computerised algorithm is used to process, quantify and present this information to give an indication of fetal movements, presentation and position. The processed information would then be displayed on an electronic display or other standard monitor.

Alternatively, a fetal ECG trace plotted in hardcopy format over a suitable time period could be employed. Typically, a printed fetal ECG trace of this form would be manually examined to determine fetal movements, presentation and position.

Figure 8:
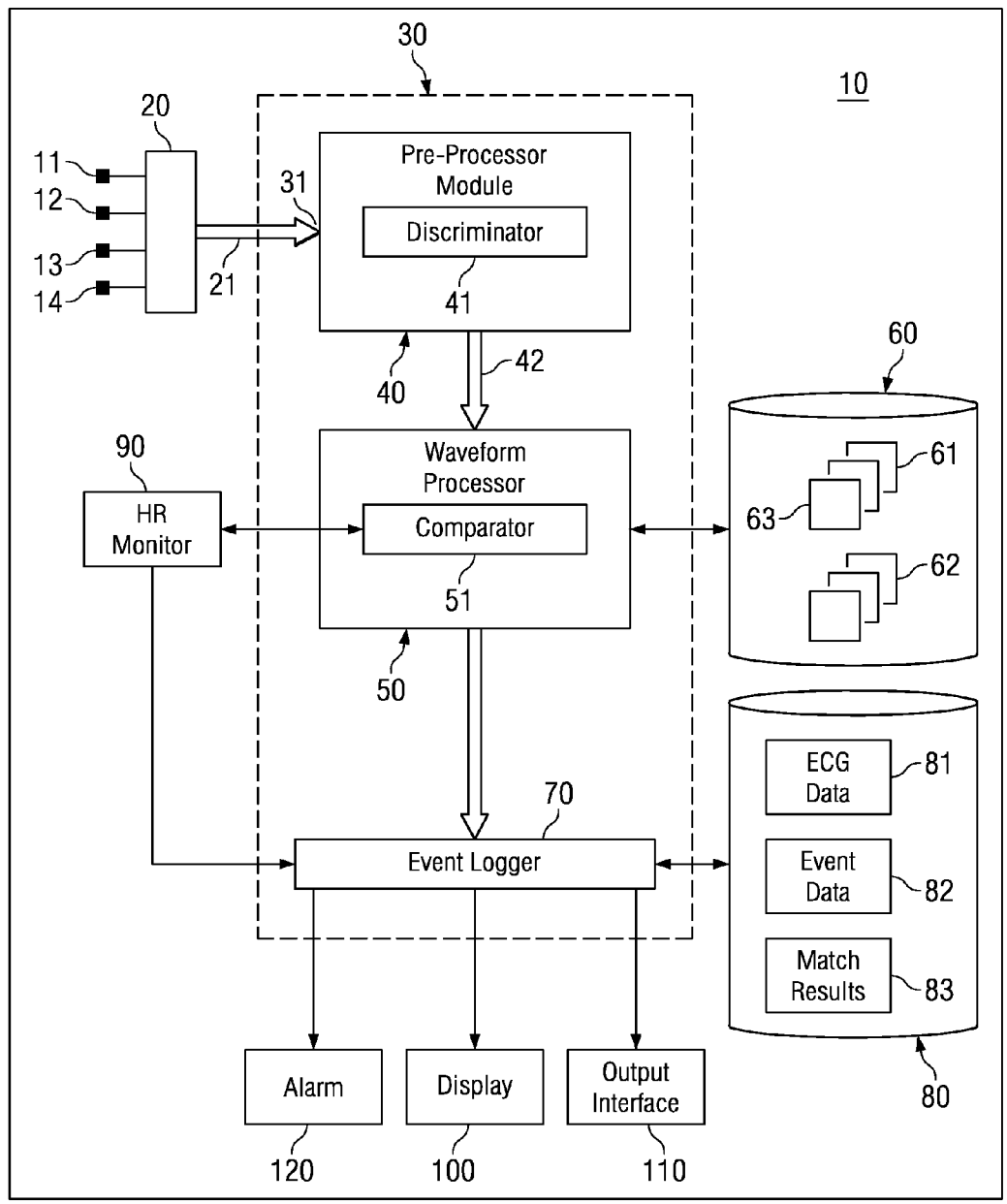
FIG. 8 is a functional block diagram of apparatus for monitoring fetal behaviour.

With reference to FIG. 8, a preferred arrangement 10 for implementing the invention is described. A plurality of electrodes 11 to 14 are positioned on the maternal abdomen at positions according to a particular preferred configuration. A number of different configurations are possible, such as that shown in FIG. 7. Although four electrodes are shown, different numbers of electrodes may be used, according to the circumstances. In one preferred embodiment, only two electrodes are used so that only one detection channel is required.

The electrodes 11 to 14 are connected to a suitable data processing device 30 preferably by way of a suitable interface 20. The interface 20 may include suitable amplifiers, analogue to digital converters and a multiplexer according to techniques well known in the art to deliver digitised ECG data 21 to the data processing device 30.

The data processing device has an input 31 generally for receiving the ECG data representing an ECG waveform from the set of electrodes 11 to 14. A pre-processor module 40 could include a discriminator 41 adapted to discriminate between fetal ECG complexes and maternal ECG complexes according to a number of possible methods. In the preferred embodiment, pre-processor module 40 identifies the maternal ECG complex waveform and subtracts it from the received data 21 according to techniques as referred to above leaving only the fetal ECG complexes in fetal ECG data 42.

A waveform processor module 50 then analyses the fetal ECG complex waveforms 42 to locate specific features therein for which comparisons may be carried out. Preferably, the specific features located correspond to the QRS complex, and in particular, the types A to D complexes illustrated in FIG. 5. Other waveform portions may also be taken into account. The waveform processor module 50 analyses a succession of such fetal ECG complexes to determine differences therebetween. In a simplest approach, the waveform processor module 50 determines a measure of difference between successive pairs of complexes. Where the change exceeds a predetermined threshold, the waveform processor module 50 determines that a fetal movement 'event' has occurred.

In another approach, the apparatus 10 includes a memory 60 containing a 'library' of fetal ECG complex templates 63. The library includes a plurality of such templates 63 each corresponding to a specific fetal spatial presentation and/or position. The library may include templates 63 in respect of each of at least cephalic presentation, breech presentation, shoulder dorsoanterior presentation and shoulder dorsoposterior presentation. The library may include templates in respect of fetal positions ROA, LOA, ROL, LOL, ROP and LOP. The library may include templates in respect of a combination of those described above for fetal presentation and fetal position.

Preferably, the templates 63 are arranged into groups or sets 61, 62 in which each set corresponds to the fetal ECG complexes above as derived from a different electrode configuration. The waveform processor 50 module includes a comparator 51 for comparing received fetal ECG complex waveforms with the set 61 or 62 of templates 63 that corresponds to the electrode configuration in use to obtain the ECG data. A suitable user input (not shown) may be provided for the user to select a configuration of electrodes in use, and thereby determine the set of templates 61 or 62 in use. Alternatively, this selection may be made automatically based on a determination of the electrodes 11 to 14 connected to the apparatus 10.

The comparator 51 may use any appropriate matching algorithm to determine a template 63 that is a best or closest match to the received fetal ECG complex waveform. When a best match is found, the fetal position and/or presentation is determined according to the identified library template 63. The comparator 51 may include threshold criteria that dictate a minimum match threshold that must be achieved in order for a match to be determined. Successive received fetal ECG waveforms are compared in similar manner. Successive best match data may be stored by an event logger 70 to record the position and/or presentation of the fetus chronologically. A movement event is logged by the event logger 70 when a change in the best match template is detected between successive fetal ECG complexes. The movement event may take place over several successive fetal ECG complexes.

The event logger 70 may store fetal ECG data 81, event data 82 and best match results 83 in a memory 80 for subsequent use, e.g. for construction of an actogram. Preferably, the apparatus 10 includes a display device 100 for displaying any or all of the data 81-83 stored by the event logger 70. Preferably, the display device 100 is adapted to display at least an event count over a fetal monitoring period. The apparatus 10 may include an electronic output interface 110 for downloading fetal ECG data 81, event data 82, actogram data and any other data obtained by the apparatus, to a remote device such as a computer system. The interface 110 may include a wired or wireless interface.

Although the preferred arrangement described in connection with FIG. 8 relates to the matching of templates 63 stored in memory 60, alternative or additional strategies may be employed by the waveform processor 50. In an implementation of the phase detection algorithm described above, the phase of a fetal ECG complex may be determined by the addition of another pre-processor module (not shown) to identify a reference baseline. This module takes as its input fetal ECG data 42 and identifies the baseline, or "DC level" which precedes and follows a fetal ECG complex, typically referred to as the isoelectric line. The waveform processor 50 removes this baseline and performs a Discrete Fourier Transform (DFT) on centrally positioned fetal ECG complexes (or time shifted variants of the complex) to detect the phase of each complex with respect to the "even" cosine function. The event logger 70 records movement events when a phase change of greater than a threshold magnitude occurs between two received fetal ECG complexes. The movement event may occur over adjacent complexes or, more likely over the duration of several successive fetal ECG complexes.

The waveform processor 50 may deploy the integration algorithm described above, by detecting changes in the amount of positive and/or negative energy of the fetal ECG complex waveforms. In an implementation of the integration algorithm described above the relative proportions of energy above or below a baseline within the fetal ECG complex may be determined by the addition of another pre-processor module (not shown) to identify a reference baseline. This module takes as its input fetal ECG data 42 and identifies the baseline, or "DC level" which precedes and follows a fetal ECG complex, typically referred to as the isoelectric line.

The waveform processor 50 identifies the period of a fetal ECG complex, hereafter referred to as T(interval), and integrates the complex over the period from the start of the fetal ECG complex to T(interval) with respect to the isoelectric line. If the result of this integration is positive, a fetal complex of type A, as illustrated in FIG. 5, is indicated. If the result of this integration is negative, a fetal complex of type B, as illustrated in FIG. 5, is indicated. If the result of this integration tends toward zero, a fetal of complex of type C or D, as illustrated in FIG. 5, is indicated. In the case that the integral result tends toward zero, a further integration is performed on the fetal ECG complex from the start of the complex to T(interval)/2 with respect to the isoelectric line. If the result of this integration is positive, a fetal complex of type C, as illustrated in FIG. 5, is indicated. If the result of this integration is negative, a fetal complex of type D, as illustrated in FIG. 5, is indicated. Other waveform portions may also be taken into account. The waveform processor 50 compares the result of integrals performed on successive fetal ECG complexes to detect changes and indicate fetal movement.

In another embodiment, the apparatus 10 may include a fetal heart rate monitor 90 coupled to the waveform processor 50. The fetal heart rate data may be stored by event Jogger 70 for later output via interface 110. The fetal heart rate data may be displayed on display 100.

An alarm unit 120 may be included for providing audio or visual feedback should the number of fetal movements within a predetermined period of time fall below a defined threshold. This could provide a warning of incorrect application/dislodgement of the electrodes or of reduced fetal activity.

Other embodiments are intentionally within the scope of the accompanying claims.

The invention claimed is:

1. Apparatus for monitoring fetal behaviour comprising:
   (i) an input configured to receive ECG data from a set of electrodes adapted to be attached to a maternal abdomen;
   (ii) a waveform pre-processor configured to identify a succession of fetal ECG complex waveforms within the received data;
   (iii) a waveform processor configured to determine differences in shapes of a succession of fetal ECG complex waveforms over time, the waveform processor including at least one of a comparator configured to match the ECG complex waveforms to a plurality of stored templates, a phase detector configured to detect a change of phase of one ECG complex relative to an adjacent ECG complex, and an integrator configured to detect changes in the amount of positive and/or negative energy in the fetal ECG complex waveforms; and
   (iv) an event logger configured to determine from the determined differences a number of fetal body movements during the period of time.

2. The apparatus of claim 1 further including a plurality of electrodes configured to be positioned at different locations on the maternal abdomen.

3. The apparatus of claim 2 in which the number of electrodes is two.

4. The apparatus of claim 1 in which the waveform preprocessor includes a discriminator configured to discriminate between maternal ECG complexes and fetal ECG complexes in a received waveform.

5. The apparatus of claim 4 in which the waveform preprocessor includes means for subtracting the maternal ECG complexes from the received waveform.

6. The apparatus of claim 1 in which the waveform preprocessor comprises means for identifying a QRS complex in the fetal ECG data.

7. The apparatus of claim 1 in which the waveform processor comprises:
   (i) a memory storing a plurality of fetal ECG complex templates each corresponding to a specific fetal spatial presentation and/or position;
   (ii) a comparator configured to compare each of the identified fetal ECG waveforms with a set of predetermined ones of the fetal ECG complex templates and determine at least one template from said set of templates that best matches each identified fetal ECG waveform.

8. The apparatus of claim 7 in which the memory stores a plurality of fetal ECG complex templates each corresponding to a specific fetal spatial presentation and/or position relative to a specific one of a plurality of different electrode configurations.

9. The apparatus of claim 7 in which the event logger records occasions on which the determined template changes.

10. The apparatus of claim 7 further including means for selecting the set of predetermined fetal ECG templates according to a preselected one of a plurality of configurations of ECG electrodes positioned on the maternal abdomen.

11. The apparatus of claim 7 in which the set of predetermined fetal ECG templates includes templates corresponding to at least cephalic presentation, breech presentation, shoulder dorsoanterior presentation and shoulder dorsoposterior presentation.

12. The apparatus of claim 1 in which the waveform processor comprises means for detecting phase changes between successive fetal ECG complex waveforms.

13. The apparatus of claim 12 in which the waveform processor comprises means for detecting phase changes of one or more predetermined magnitudes between successive fetal ECG complex waveforms.

14. The apparatus of claim 12 in which the event logger records occasions on which a phase change occurs.

15. The apparatus of claim 1 in which the waveform processor is adapted to determine differences in fetal complex waveforms by detecting change in the relative proportions of energy of a fetal ECG complex waveform above and below a baseline reference.

16. The apparatus of claim 15 in which the baseline reference is the isoelectric line of a fetal ECG complex.

17. The apparatus of claim 15 in which the reference is derived from a previous or average fetal ECG complex waveform.

18. The apparatus of claim 1 further including a display configured to display a count of the number of fetal body movements detected.

19. The apparatus of claim 1 wherein the waveform processor further includes a fetal heart rate monitor.

20. The apparatus of claim 1 further including an alarm configured to indicate if the number of fetal body movements during a period of time falls below a predetermined threshold.

21. The apparatus of claim 1 further including a memory configured to store fetal body movement event data and an electronic interface configured to download said event data to a remote device.

22. A method for monitoring fetal behaviour comprising:
   (i) obtaining fetal ECG data over a period of time;
   (ii) identifying a succession of fetal ECG complex waveforms within the data;
   (iii) determining differences in the shapes of a succession of fetal ECG complex waveforms over time, said step of determining differences including at least one of the steps of matching the ECG complex waveforms to a plurality of stored templates, detecting a change of phase of one ECG complex relative to an adjacent ECG complex, and detecting changes in the amount of positive and/or negative energy in the fetal ECG complex waveforms by integration; and
   (iv) determining from the determined differences a number of fetal body movements during the period of time.

23. The method of claim 22 in which step (i) comprises obtaining fetal ECG data from a plurality of electrodes positioned at different locations on the maternal abdomen.

24. The method of claim 23 in which step (ii) includes the step of discriminating between maternal ECG complexes and fetal ECG complexes in a received waveform.

25. The method of claim 24 in which step (ii) includes subtracting the maternal ECG complexes from the received waveform.

26. The method of claim 22 in which step (ii) comprises identifying a QRS complex in the fetal ECG data.

27. The method of claim 22 in which step (iii) includes:
   (i) comparing each of the identified fetal ECG waveforms with a set of predetermined fetal ECG complex templates; and
   (ii) determining at least one template from said set of templates that best matches each identified fetal ECG waveform.

28. The method of claim 27 in which step (iv) comprises determining the number of successive occasions on which the determined template changes during the period of time.

29. The method of claim 27 in which the set of predetermined fetal ECG templates is selected according to a preselected one of a plurality of configurations of ECG electrodes positioned on the maternal abdomen.

30. The method of claim 27 in which the set of predetermined fetal ECG templates includes templates corresponding to at least cephalic presentation, breech presentation, shoulder dorsoanterior presentation and shoulder dorsoposterior presentation.

31. The method of claim 27 in which step (iii) comprises detecting phase changes between successive fetal ECG complex waveforms.

32. The method of claim 22 in which step (iii) comprises detecting phase changes of one or more predetermined magnitudes between successive fetal ECG complex waveforms.

33. The method of claim 31 in which step (iv) comprises determining the number of successive occasions on which a phase change occurs during the period of time.

34. The method of claim 22 in which the differences determined in step (iii) comprise change in the relative proportions of energy of a fetal ECG complex waveform above and below a baseline reference.

35. The method of claim 34 in which the baseline is the isoelectric line of a fetal ECG complex.

36. The method of claim 34 in which the reference is derived from a previous or average fetal ECG complex waveform.

37. The method of claim 22 further including the step of displaying or logging a cumulative count of the number of fetal body movements within the period of time.

38. The method of claim 22 further including the step of monitoring fetal heart rate.

39. The method of claim 22 further including the step of indicating an alarm condition if the number of fetal body movements during the period of time falls below a predetermined threshold.

* * * * *